US008460687B1

(12) United States Patent
Volynsky et al.

(10) Patent No.: US 8,460,687 B1
(45) Date of Patent: Jun. 11, 2013

(54) PEELING COMPOSITIONS

(75) Inventors: Yelena Michelle Volynsky, Tarzana, CA (US); Vartan Libardian, Granada Hills, CA (US)

(73) Assignee: Cosmoceutical Research Center, Van Nuys, CA (US)

( * ) Notice: Subject to any disclaimer, the term of this patent is extended or adjusted under 35 U.S.C. 154(b) by 195 days.

(21) Appl. No.: 12/801,070

(22) Filed: May 20, 2010

Related U.S. Application Data

(60) Provisional application No. 61/270,261, filed on Jul. 7, 2009.

(51) Int. Cl.
*A61K 8/00* (2006.01)
*A61K 8/18* (2006.01)
*A61K 8/02* (2006.01)
*A61Q 17/04* (2006.01)

(52) U.S. Cl.
USPC .......................................... 424/401; 424/59

(58) Field of Classification Search
USPC ................................... 424/401, 59
See application file for complete search history.

(56) References Cited

U.S. PATENT DOCUMENTS

| | | | |
|---|---|---|---|
| 4,874,361 A | 10/1989 | Obagi | |
| 5,116,605 A | 5/1992 | Alt | |
| 5,434,144 A | 7/1995 | Kasting et al. | |
| 5,536,499 A | 7/1996 | Znaiden et al. | |
| 5,665,364 A | 9/1997 | McAtee et al. | |
| 5,716,625 A | 2/1998 | Hahn et al. | |
| 5,811,111 A | 9/1998 | McAtee et al. | |
| 6,139,850 A | 10/2000 | Hann et al. | |
| 6,761,896 B1 * | 7/2004 | Znaiden et al. | 424/401 |
| 7,189,406 B1 | 3/2007 | Gross | |
| 7,288,263 B2 * | 10/2007 | Boxrud | 424/401 |
| 7,439,214 B2 | 10/2008 | Utz et al. | |
| 2002/0082293 A1 * | 6/2002 | Ancira | 514/460 |
| 2004/0092482 A1 * | 5/2004 | Gupta | 514/62 |
| 2006/0127429 A1 * | 6/2006 | McCartt et al. | 424/401 |
| 2007/0154419 A1 | 7/2007 | Hattendorf et al. | |

OTHER PUBLICATIONS

Van Scott EJ, Yu RJ.,"Alpa hydroxy acids: procedures for use in clinical practice", Cutis,1989,pp. 222-228, vol. 43.
Dendougui, F. et al. "In vitro analysis of binding capacities of calcium to phytic acid in different food samples" European food research and technology, Sep. 2004. pp .409-415, vol. 219, No. 4.
Okubo, K. et al.,"Binding of phytic acid to glycinin", Cerial Chemistry, Jul.-Aug. 1976. pp. 513-524. vol. 53. No. 4.
Graf et al., "Iron-catalyzed hydroxyl radical formulation. Stringent requirement for free iron coordination site." Journal of Biological Chemistry Mar. 1984. pp. 3620-3624. vol. 259.
Graf E. et al."Phytic acid. A natural antioxidant." Journal of Biological Chemistry Aug. 25, 1987, pp. 11647-11650, vol. 262, No. 24.

* cited by examiner

*Primary Examiner* — Fereydoun G Sajjadi
*Assistant Examiner* — Courtney Brown
(74) *Attorney, Agent, or Firm* — Inna Reichstein

(57) ABSTRACT

The present invention discloses cosmetic compositions based on phytic acid and used for skin resurfacing, treating hyper pigmentation, control sebum production, for pore size reduction and combating acne and a method of application. The trichloroacetic acid can be added to the composition, containing phytic acid for more deep peels. The compositions and the methods of application of the composition containing phytic acid and the composition, containing trichloroacetic acid and phytic acid are claimed.

3 Claims, No Drawings

PEELING COMPOSITIONS

CROSS REFERENCE TO RELATED APPLICATIONS

The Applicant claims priority of U.S. Provisional application No. 61/270,261 filed Jul. 7, 2009

FIELD OF THE INVENTION

The present invention relates to dermatological compositions and methods for applying the compositions to skin and more particular to peeling compositions and methods for resurfacing, treating hyper pigmentation, control sebum production, for pore size reduction and combating acne.

BACKGROUND OF THE INVENTION

Skin renewal can be achieved by using chemical peels. Chemical peels employ a variety of caustic chemicals to selectively destroy several layers of skin. They are divided into three types: superficial, medium depth and deep peelings. The type of peel depends on the strength of the used chemical and how deeply it penetrates. Superficial peels are used for fine wrinkles, sun damage, acne and rosacea. Superficial peels damage the outer layer of the skin. Well known superficial chemical peels are AHAs (alpha hydroxyl acids). These chemicals work on the epidermis by reducing the thickness of hyperkeratosis in the stratum corneum by decreasing corneocyte adhesion (Van Scott E J. YU R J, Alpha hydroxy acids procedures for use in clinical practice, Cutis (1989) 43: 222-8)

The recovery is rapid and usually consists of minor flaking and redness for several days. Results of AHA peel are temporary and periodic treatments are recommended to maintain the results.

Glycolic acid is most frequently used as superficial peeling agent at 50% weight to 70% weight concentration. It may be used to treat many lesions that are predominantly in the epidermis or superficial dermis, including fine wrinkles, actinic keratoses, melasma, lentigines, and seborrheic keratoses. To achieve consistently good results, a serious of three to four repeated peels at 3 to 4 weeks intervals may improve the efficacy by producing additive effects and minimizing complications. Glycolic acid at 50% weight to 70% weight may cause dermal necrosis, comparable to 35% weight trichloroacetic acid (TCA), if left in for a long period of time.

The compositions for applying to skin comprising TCA are generally known in the art U.S. Pat. No. 4,874,361 A (Obagi, Zein E.) claims a method of treating human skin by applying trichloroacetic acid to the damaged areas.

U.S. Pat. No. 5,599,546 A (Klein, Martin E.) claims a method of treating skin by applying an aqueous mixture comprising trichloroacetic acid.

U.S. Pat. Nos. 5,716,625 A and 6,139,850 A (Hahn, Gary S. et al.) claim topical formulations comprising an irritant ingredient such as trichloroacetic acid.

U.S. Pat. No. 7,189,406 B1 (Gross. Dennis) is directed to a method for treating skin. The method includes applying to the skin a first dermatological liquid composition comprising an effective amount of a skin renewal stimulating acid such as trichloroacetic acid.

The recent research shows the possibility for use of phytic acid for skin treatment.

U.S. Pat. No. 5,116,605 A (Alt; John P.) claims a topical application for treating acne comprising inositol and phosphoric acid (see Cl. 1).

U.S. Pat. No. 5,434,144 A (Kasting; Gerald B. et al.) discloses a composition for treating wrinkles comprising phytic acid and polyols (see Cl. 1).

U.S. Pat. No. 5,536,499 A (Znaiden; Alexander P. et al.) discloses cosmetic compositions for increasing the strength and firmness of the skin. The composition includes phytic acid (see abst.; Cl. 1-5).

U.S. Pat. No. 5,665,364 A and No. 5,811,111 A (McAtee; David Michael et al.) claim a composition for treating acne, skin lesions, blemishes and other skin imperfections. The composition includes phytic acid (see abst.; Cl. 12 for U.S. Pat. No. 5,665,364 and col. 9.1.1 and col. 10.1.1 for U.S. Pat. No. 5,811,111).

U.S. Pat. No. 7,439,214 B2 (Utz, Ferdinand) claims a cosmoceutical composition comprising phytic acid or trichloracetic acid as active ingredients (see c1.1-4).

US application No. 2007/0154419 A1 (Hattendorf; Judy et al.) discloses a application corrective compositions that can include phytic acid. The peeling agents such as trichloroacetic acid can be used (see [0054]. [0062}, [0084], and [0099]).

However, none of the references suggests the use of the compositions and the methods of applying them to the skin disclosed in details below in the disclosure and in the attached claims.

In view of limitations and shortcomings of the prior art compositions and methods it should be apparent that there still exists a need in the art for effective products for skin treatment that can be applied to the skin in a safe way.

SUMMARY OF THE INVENTION

The present invention is directed to peeling compositions based on phytic acid and methods for treating the skin using these compositions. The first aspect of the invention is a superficial peeling cosmetic composition comprises a phytic acid and a glycol. The glycol can be ethoxydiglycol, pentylene glycol or mixture of ethoxydiglycol and pentylene glycol. The concentration of the phytic acid can be from about 15% by weight to about 50% by weight. The another aspect of the invention is a method for treating and resurfacing skin for controlling sebum production, pore size reduction, tyrosinase inhibiting activity and acne treatment using the above composition that includes applying to a clean skin a phytic acid and glycols to form a cosmetic layer, exposing the layer to a light for a limited period of time, washing the skin with water and finishing the treatment with a cosmetic regiment chosen according to the skin problems. The exposition time can vary from about 1 to about 15 min.

It is still another aspect of the invention that is includes a superficial and deep chemical peeling composition comprising a solution of a phytic acid, a trichloroacetic acid and a glycol. The concentration of the phytic acid is about 50% by weight and the concentration of the trichloroacetic acid is from about 5% by weight to about 50% by weight. The glycol can be ethoxydiglycol. It is yet another aspect of the invention to provide a method for deeper peel treatment of the skin using the second composition that includes applying to a clean skin the composition comprising a solution of a phytic acid, a trichloroacetic acid and a glycol to form cosmetic layers, exposing a layer to a light for a limited period of time, applying a wet article to the skin for a limited period of time and repeating the procedure according to the skin conditions to form a number of layers, washing the skin with water and finishing the treatment with a cosmetic regiment chosen according to the skin problems. The exposition time of each layer is from about 1 to 1.5 minutes and exposition of a wet article on the top of each layer is up to about 30 sec. The number required layers depends on the depth of the peel and a frost appearing on the skin. The wet article is a cloth, a napkin or towel.

With the foregoing and other objects, advantages and features of the invention that will become hereinafter apparent, the nature of the invention may be more clearly understood by reference to the following detailed disclosure of the invention and the appended claims.

DETAILED DESCRIPTION OF THE INVENTION

Although certain presently prepared embodiments of the invention have been described herein, it will be apparent to those skilled in the art to which the invention pertains that variations and modifications of the described embodiments may be made without departing from the spirit and scope of the invention.

All percentages and ratios used herein are by weight of the total composition and all measurements made at 25.degree.C. unless otherwise designated. All percentages are on a weight/weight basis.

In one embodiment, there is disclosed a composition, including water, a glycol, phytic acid. In one embodiment, the composition has a pH of less than about 1.

In one embodiment, there is a composition, including water, a glycol, phytic acid and trichloroacetic acid. In one embodiment, the composition has a pH in a range of about 0.56 to about of 0.75. In another embodiment, the composition has a pH in a range of about 0.55 to about 0.80. In another embodiment, the composition has a pH in a range of about 0.62 to about 0.80. Phytic acid molecular formula $C_6H_{18}O_{24}P_6$ and molar mass 660.04 $gmol^{-1}$ known as inisitol hexakisphosphate (IP6) or phytate when in salt form is the principal storage form of phosphorous in many plant tissues, especially bran and seeds.

Phytic acid is a strong chelator of important minerals such as calcium, magnesium, iron, and zinc, and can therefore contribute to mineral deficiencies in people whose diets rely on these foods for their mineral intake. Binding of calcium with phytic acid depends on PH (Dendougui, Ferial; Schwedt, Georg (2004). "In vitro analysis of binding capacities of calcium to phytic acid in different food samples". "European Food Research and Technology 219, doi: 10.1007/S 00217-004-0912-7".

Phytic acid is an excellent anti-oxidant, unique free radical inhibitor, enormous inherent buffering properties, binds proteins, involved in cellular control systems, bio-active stable.

An aqueous solution has an intense acidity, pH=0.9 at 66 g/l and pH 2.68 at 0.66 g/l. Phytic acid would react with a polyvalent cation, such as Ca,Zn,Fe and thus form an insoluble compound at a neutral or high pH value region.

Phytic acid precipitates most proteins at low pH in the absence of cations by binding to protonated basic residues and at high pH in the presence of cations, presumably by forming a ternary protein-metal-phytate complex (Okubo, K. D., Myers and G. A. Jacobucci, Cereal Chem. 53:513, 1976).

Phytic acid also is a good antioxidant due to formation of a complex with Fe that lacks iron-coordinated water and thus is unable to catalyze the formation of hydroxyl radicals in the Fenton reaction and Haber-Weiss cycle (Graf, E., J. R. Mahoney, R. G. Bryant and J. W. Eaton, submitted to J. Biolog. Chem.). It inhibits the oxidation of ascorbic acid (vitamin C), stabilizes sorbic acid and prevents peroxidation and hydrolysis of fats and oils and with mixture of tocopherol acetate (vitamin E) also proven useful for the protection sutoxidation of methyl oleate and other lipids. Graf E, Empson K L, Eaton J W, J. Biol. Chem., 1987, Aug. 25; 262(24); 11647-50

In one embodiment the composition includes about 50 percent by weight of phytic acid, and glycols in an inert liquid. The preferred range of concentration will be about 50% As used herein the term "composition" means a composition useful for topical application to the skin of a human.

Suitable glycols include, but are not limited to dihydric alcohols, propylene glycol, butylene glycol, ethylene glycol, pentylene glycol, and mixtures and blends thereof. Suitable glycols also include, but are not limited to alkoxydiglycols, for example methoxydiglocol, ethoxydiglycol, propoxydiglycol, butoxydiglycol), and $C_1$ to $C_4$ glycols.

In one embodiment, a suitable glycol is ethoxydiglycol, commercially available from Gattefosse, Canada, under the name Transcutol.

In another embodiment, a suitable glycol is pentylene glycol, commercially available from Evonik Degussa under the name 1,2 Pentanediol, Germany.

Suitable phytic acid is commercially available from Premier, N J.

Composition having pH less than about 1 may have exfoliating properties.

In one embodiment, the composition is suitable for application to human skin (e.g., face and body). A method of exfoliating skin includes applying a quantity of a composition. A composition is applied to a whole face or a portion or area of the skin and of a body. Once applied, the composition is retained or left on the skin for a certain period of time, depending on type of skin, but no more than total of 15 minutes. The number of layers can be increased, depending of the type and skin conditions. After time of 1 to 15 minutes, depending of a type of the skin, leaving composition on the skin, the composition is removed with lukewarm water.

Various skin-renewal stimulating acids may be combined together, and simple tests can be used to evaluate their efficacy and side effects, for incorporation into cosmetics suitable for application to the skin.

In another embodiment, the composition includes about 15 percent, by weight of trichloroacetic acid ($CCl_3COOH$; sometimes abbreviated herein as TCA) and less than 50 percent by weight of phytic acid, herein abbreviated as PHA 15%.

In another embodiment, the composition includes about 30 percent by weight of TCA and less 25 percent of phytic acid, herein abbreviated as PHA 30%.

In another embodiment, the composition includes 50 percent by weight of TCA and less than 10 percent by weight of phytic acid, herein abbreviated as PHA 50%.

Suitable compositions include the following by weight:
1-40% glycol
0-50% TCA
1-50% Phytic acid
10-70% Water Suitable trichoroacetic acid is commercially available from Spectrum, CA under the name TCA.

One preferred method of application is via single-use pads. The pads are disposable, convenient and sanitary. Pads suitable for use in the current invention may be made of woven or nonwoven cloth or brush. Natural or synthetic fibers may be used. Preferred pads are made of cotton or a cotton/synthetic blend and or synthetic brush.

Other preferred methods of application include cotton balls and cotton-tipped applicators moistened with the compositions of the present invention.

In another embodiment the composition may includes from 15% to 50% of phytic acid by weight.

In another embodiment, the composition includes trichloroacetic acid to increase an exfoliating activity.

In another embodiment, the concentration of the trichloroacitic acid can be from about 5% to 50% by weight in combination with phytic acid and glycol.

In another embodiment, a suitable glycol includes ethoxydiglycol.

One preferred method of application is via single-use pads containing a calibrated amount of the compositions of the present invention. Pads are disposable, convenient and sanitary. Pads suitable for use in the current invention may be made of woven or nonwoven cloth, paper, sponges. Natural or synthetic fibers may be used. Preferred pads are made of cotton or a cotton/synthetic blend. They may comprise a single layer, or multiple layers.

Other preferred methods of application include cotton balls and cotton-tipped applicators moistened with the compositions of the present invention.

In one embodiment, the composition is suitable for application to human skin (e.g., face and body). A method of exfoliating skin includes applying a quantity of a composition. A composition is applied to a whole face or a portion or area of the skin, and of a body. Once applied, the composition is retained or left on the skin for a period of time, depending on type of skin and concentration of TCA. Application of a wet article to the skin for a limited period of time, about half of a minute will increase a burning sensation, noticeable by the patient, but tolerable. A number of layers of the composition and following application of a wet article depends on desirable results. The exposition of each layer of the composition on the skin should be in a range of from about 1 minute to about 1.5 minutes.

One preferred method of application includes a wet cloth, a napkin, a towel.

The invention herein is a result of our discovery that, unlike in regular skin peel treatments, involving deep peeling with high concentration of the acid, can be done without additional sedation of patient. The pain is tolerable and peel is controlled. The invention is further illustrated by the following examples.

Example 1

A solution, containing about 50-51% by weight phytic acid was prepared in this example in combination with 10% by weight of ethoxydiglycol, and 5% by weight of pentylene glycol, with mixing, to form a phytic acid concentrate.

Unlike other superficial chemical peels, where the method usually started with cleaning the skin, using ethanol to degrease the skin and to remove makeup and debris, this invention does not required such a preparation. A simple cleaning with a cleanser can be used.

Following the cleaning step, the facial skin, or other parts, like back skin of the body was then treated with the phytic acid solution, hereinafter called phytic treatment concentrate (PTC).

The phytic treatment concentrate (PTC) was topically applied by hands in a single uniform coating to the entire area being treated, at ambient temperature, about 20-25° C.

The phytic treatment concentrate (PTC) was allowed to air dry on the treated skin over a period of about 2 to 4 minutes for the first time depending on skin type: 1-2 minutes for dark skin and 3-4 minutes for light skin. The total exposure to the skin should not be more than 10 to 15 minutes, depending on skin type.

A typical patient may or may not experience some tingle or light stinging sensation in the treated area after about one minute. This sensation typically reached a peak in about two minutes after the phytic treatment concentrate was first applied, and goes itself away. No superficial anesthesia is needed.

After the phytic treatment concentrate had air dried, the treated facial skin was then washed with lukewarm water, by the patients's hands, washing the treated areas at a sink. There were no erythema or edema during after treatment period. In contrast to many prior art peeling techniques, the typical patient was able resume normal work and social activities immediately. On the other hand, it was clearly evident that skin treated with phytic treatment concentrate looked tighter, shiny and lighter.

In patients with acne vulgaris, treatment with phytic treatment concentrate prepared according to this invention rapidly brings this skin disorder under control, by providing rapid extrusion of comedones, both blackheads and whiteheads, in comedonal acne, and by providing resorption of pustules in inflammatory acne. In patients with acne caused shallow scaring, the treatment was also beneficial for improving the appearance of skin, by providing skin with smoother, more uniform texture, by decreasing pore size of the skin.

In patients with photo damaged, wrinkled, blotchy facial skin, the phytic treatment concentrate, according to the invention likewise provided a significant improvement in appearance, even better than typically achieved with alpha-hydroxy acid peels. The benefits included lightening of hyperpigmented areas, such as age or liver spots, formation of smooth, unblemished skin having uniform texture and color, removal of comedones, regulating sebum production and formation of a smoother, more elastic skin. The application of phytic treatment concentrate was repeated with some patients, as necessary or as desired, at 3 days to 1 week intervals. With repeated applications, the same events occurred except that the result is better. Also the better results were achieved with the number of 3 to 10 applications in a period of 2 weeks. After the procedure Cosmoceutical Research Center (CRC) system of products is used depending on a skin problem.

Example 2

A chemical peeling solution was prepared by mixing of about 30% by weight of TCA, of 35% by weight of phytic acid and of 35% by weight of ethoxydiglycol. A face of each patient in age of 35 to 55 years old was pasted with the peeling composition, hereinafter called PHA. Following the cleaning step, the PHA was topically applied with a brush, swabbing with solution at ambient temperature, about 20-25° C. on entire face for 1 to 1.5 minutes. A typical patient experienced some stinging and burning sensations in the treated area after about one minute. A fan was used to cool and to subside a burning sensation. In one and a half minutes after PHA treatment a wet article, such as towel, cloth or napkin was applied for 30 sec. The number of layers of each application of PHA and wet article depends on desirable result, which was an appearance of frost, white cover on the skin, showing protein precipitation. Unlike other chemical peels, including thrichloroacetic acid (TCA), the present invention doesn't require a sedation and can be controlled.

Minimal scaling or peeling of the treated skin was evident until about 2 to about 5 days after the treatment. Erythema and edema were minimal or were not appeared. An observation was conducted by means of a digital camera. The observation has revealed a disappearance of shallow wrinkles and a brightness of the skin for all the persons under the test. There were no side effects and the benefits include lightening of hyperpigmented areas, formation of smooth unblemished skin, having uniform texture and color, removal of comedones.

Further, no side effects, for example, red spots, pigmentation, scars and other imperfections were recognized for all the tested patients.

Example 3

A chemical peeling solution was prepared by mixing, about 60% by weight of TCA, 10% by weight of phytic acid and 10% by weight of ethoxydiglycol.

A face of each patient in age of 35 to 55 years old was pasted with the peeling composition, hereinafter called PHA. Following the cleaning step, the PHA was topically applied with a brush, swabbing with solution at ambient temperature, about 20-25° C. on entire face for 1 to 1.5 minutes. A typical patient experienced some stinging and burning sensation in the treated area after about one minute and this was followed by using fan to cool and burning sensation subsided. After one and a half minutes after PHA was applied a wet article, including towel, cloth or napkin was applied for 30 sec. The number of layers of each application of PHA and wet art depends of desirable result, which was an appearance of frost, white cover on the skin, showing protein precipitation. Unlike other chemical peels, including thrichloroacitic acid (TCA), the present invention doesn't require a sedation and can be controlled.

Minimal scaling or peeling of the treated skin was evident until about 2 to about 5 days after the treatment. Erythema and edema were minimal or were not appeared at all. Further, no side effects, for example, red spots, pigmentation, scars and so on were recognized for all the patients under test.

Example 4

A chemical peeling solution was prepared by mixing, about 50% by weight of TCA, 5% by weight of phytic acid and about 4% by weight of ethoxydiglycol. A face of each 10 patients in the fifties was pasted with the peeling composition, hereinafter calls PHA. Following the cleaning step, the PHA was topically applied with a brush, swabbing with solution at ambient temperature, about 20-25° C. on entire face for 1 to 1.5 minutes. A typical patient experiences a burning sensation in the treated area after about half a minute and this was followed by using a fan to cool the burning area and to subside a burning sensation. After one and a half minutes after PHA treatment a wet article including a towel, a cloth or a napkin was applied for 30 sec. After an appearance of frost, white cover on the skin, showing protein precipitation, unfrosted areas can be treated separately, without touching other areas.

Unlike other chemical peels, including thrichloroacitic acid (TCA), the present invention doesn't requires a sedation and can be controlled. There is no experience in the past with 50% TCA as a chemical peeling agent was done before without sedation, compare with this invention.

A peeling of the treated skin was evident until about 2 to about 5 days after the treatment. A peeling of the treated areas was gentle and even.

Erythema and edema were minimal or were not appeared.

Further, no side effects, for example, red spots, pigmentation, scars and so on were recognized for all the patients under test.

What is claimed is:

1. A superficial and deep chemical peeling composition comprising a solution of phytic acid having the concentration of about 15% to about 50% by weight, trichloroacetic acid and ethoxydiglycol.

2. The composition of claim 1 wherein the concentration of phytic acid is about 35% by weight.

3. The composition of claim 1, wherein the concentration of the trichloroacetic acid is from about 5% by weight to about 50% by weight.

* * * * *